US010080868B2

(12) United States Patent
Sina

(10) Patent No.: US 10,080,868 B2
(45) Date of Patent: Sep. 25, 2018

(54) CATHETER SYSTEMS WITH A BLOCKING MECHANISM AND METHODS FOR BYPASSING AN OCCLUSION IN A BLOOD VESSEL

(71) Applicant: Invatec S.P.A., Roncadelle, BS (IT)

(72) Inventor: Achille Sina, Sarezzo (IT)

(73) Assignee: Invatec S.P.A., Roncadelle (IT)

( * ) Notice: Subject to any disclaimer, the term of this patent is extended or adjusted under 35 U.S.C. 154(b) by 329 days.

(21) Appl. No.: 15/135,039

(22) Filed: Apr. 21, 2016

(65) Prior Publication Data

US 2016/0235948 A1    Aug. 18, 2016

Related U.S. Application Data

(62) Division of application No. 13/967,707, filed on Aug. 15, 2013, now Pat. No. 9,320,874.

(51) Int. Cl.
*A61M 25/01* (2006.01)
*A61M 25/09* (2006.01)
(Continued)

(52) U.S. Cl.
CPC ......... *A61M 25/0194* (2013.01); *A61B 17/22* (2013.01); *A61M 25/0074* (2013.01);
(Continued)

(58) Field of Classification Search
CPC .............. A61M 25/01; A61M 25/0074; A61M 25/0194; A61M 25/09; A61M 25/09041;
(Continued)

(56) References Cited

U.S. PATENT DOCUMENTS 4,552,554 A    11/1985 Gould et al.
4,774,949 A    10/1988 Fogarty
(Continued)

FOREIGN PATENT DOCUMENTS

EP    0371486    6/1990
EP    1765193    10/2012
(Continued)

OTHER PUBLICATIONS

EP Application No. 14180756.0, Extended European Search Report, dated Feb. 9, 2015.
(Continued)

*Primary Examiner* — Todd J Scherbel
(74) *Attorney, Agent, or Firm* — Medler Ferro Woodhouse & Mills PLLC

(57) ABSTRACT

A catheter for use with a subintimal reentry guidewire includes a proximal portion having a proximal guidewire lumen and a proximal inflation lumen, a distal portion having a distal guidewire lumen and a distal inflation lumen, and an intermediate portion disposed between the proximal portion and the distal portion and having an intermediate inflation lumen in fluid communication with the proximal and distal inflation lumens. The intermediate portion is devoid of a guidewire lumen. A blocking mechanism disposed in the distal portion of the catheter is transformable from a non-blocking configuration in which a guidewire is free to translate through the distal guidewire lumen and a blocking configuration in which a guidewire disposed in the distal guidewire lumen is prevented from translating through the distal guidewire lumen.

27 Claims, 12 Drawing Sheets

(51) Int. Cl.
*A61M 25/10* (2013.01)
*A61M 25/00* (2006.01)
*A61B 17/22* (2006.01)

(52) U.S. Cl.
CPC .. *A61M 25/0138* (2013.01); *A61M 25/09041* (2013.01); *A61M 25/104* (2013.01); *A61B 2017/22001* (2013.01); *A61B 2017/22044* (2013.01); *A61B 2017/22095* (2013.01); *A61M 2025/0018* (2013.01); *A61M 2025/018* (2013.01); *A61M 2025/0177* (2013.01); *A61M 2025/0197* (2013.01); *A61M 2025/09125* (2013.01)

(58) Field of Classification Search
CPC ...... A61M 25/0905; A61M 2025/0079; A61M 2025/0177; A61M 2025/0197; A61M 2025/09008; A61M 2025/09116; A61M 2025/09125; A61M 2025/0018; A61B 17/32; A61B 17/3417; A61B 17/3421; A61B 17/3439; A61B 2017/22094; A61B 2017/22095; A61B 2017/3441
See application file for complete search history.

(56) References Cited

U.S. PATENT DOCUMENTS

| | | | |
|---|---|---|---|
| 4,932,959 A | 6/1990 | Horzewski et al. |
| 4,936,310 A | 6/1990 | Engstroem et al. |
| 5,085,636 A | 2/1992 | Burns |
| 5,336,184 A | 8/1994 | Teirstein |
| 5,707,389 A | 1/1998 | Louw et al. |
| 5,830,222 A | 11/1998 | Makower |
| 5,916,194 A | 6/1999 | Jacobsen et al. |
| 5,947,994 A | 9/1999 | Louw et al. |
| 6,059,484 A | 5/2000 | Grieve |
| 6,068,638 A | 5/2000 | Makower |
| 6,071,292 A | 6/2000 | Makower et al. |
| 6,081,738 A | 6/2000 | Hinohara et al. |
| 6,159,225 A | 12/2000 | Makower |
| 6,178,968 B1 | 1/2001 | Louw et al. |
| 6,190,353 B1 | 2/2001 | Makower et al. |
| 6,203,524 B1 | 3/2001 | Burney et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,563 B1 | 5/2001 | White et al. |
| 6,231,587 B1 | 5/2001 | Makower et al. |
| 6,235,000 B1 | 5/2001 | Milo et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,375,615 B1 | 4/2002 | Makower et al. |
| 6,379,319 B1 | 4/2002 | Garibotto et al. |
| 6,432,127 B1 | 8/2002 | Kim et al. |
| 6,447,477 B2 | 9/2002 | Burney et al. |
| 6,458,098 B1 | 10/2002 | Kanesaka |
| 6,508,824 B1 | 1/2003 | Flaherty et al. |
| 6,511,458 B2 | 1/2003 | Milo et al. |
| 6,514,217 B1 | 2/2003 | Selmon et al. |
| 6,544,230 B1 | 4/2003 | Flaherty et al. |
| 6,579,311 B1 | 6/2003 | Makower |
| 6,602,241 B2 | 8/2003 | Makower et al. |
| 6,655,386 B1 | 12/2003 | Makower et al. |
| 6,669,709 B1 | 12/2003 | Cohn et al. |
| 6,709,444 B1 | 3/2004 | Makower et al. |
| 6,719,725 B2 | 4/2004 | Milo et al. |
| 6,726,677 B1 | 4/2004 | Makower et al. |
| 6,746,464 B1 | 6/2004 | Makower et al. |
| 7,004,173 B2 | 2/2006 | Sparks et al. |
| 7,059,330 B1 | 6/2006 | Makower et al. |
| 7,066,914 B2 | 6/2006 | Andersen |
| 7,141,041 B2 | 11/2006 | Seward |
| 7,179,270 B2 | 2/2007 | Makower et al. |
| 7,316,655 B2 | 1/2008 | Garibotto et al. |
| 7,357,794 B2 | 4/2008 | Makower et al. |
| 7,534,223 B2 | 5/2009 | Boutilette et al. |
| 7,606,615 B2 | 10/2009 | Makower et al. |
| 7,637,870 B2 | 12/2009 | Flaherty et al. |
| 7,729,738 B2 | 6/2010 | Flaherty et al. |
| 7,833,197 B2 | 11/2010 | Boutilette et al. |
| 7,854,727 B2 | 12/2010 | Belsley |
| RE42,049 E | 1/2011 | Schroeder et al. |
| 7,878,986 B2 | 2/2011 | Jen et al. |
| 7,938,819 B2 | 5/2011 | Kugler et al. |
| 8,083,727 B2 | 12/2011 | Kugler et al. |
| 8,172,863 B2 | 5/2012 | Robinson et al. |
| 8,202,246 B2 | 6/2012 | Kugler et al. |
| 8,221,357 B2 | 7/2012 | Boutillette |
| 8,226,566 B2 | 7/2012 | Nita |
| 8,241,311 B2 | 8/2012 | Ward et al. |
| 8,257,382 B2 | 9/2012 | Rottenberg et al. |
| 8,323,261 B2 | 12/2012 | Kugler et al. |
| 8,337,425 B2 | 12/2012 | Olson et al. |
| 8,388,876 B2 | 3/2013 | Boutilette et al. |
| 8,460,254 B2 | 6/2013 | Belsley |
| 8,486,022 B2 | 7/2013 | Ludwig et al. |
| 8,496,679 B2 | 7/2013 | Robinson et al. |
| 8,512,310 B2 | 8/2013 | Kugler et al. |
| 8,535,245 B2 | 9/2013 | Jen et al. |
| 8,556,857 B2 | 10/2013 | Boutilette |
| 9,320,874 B2 * | 4/2016 | Sina ............... A61M 25/0074 |
| 2001/0000041 A1 | 3/2001 | Selmon et al. |
| 2002/0072706 A1 | 6/2002 | Hiblar et al. |
| 2004/0167554 A1 | 8/2004 | Simpson et al. |
| 2005/0021003 A1 | 1/2005 | Caso et al. |
| 2005/0143770 A1 | 6/2005 | Carter et al. |
| 2005/0171478 A1 | 8/2005 | Selmon et al. |
| 2006/0094930 A1 | 5/2006 | Sparks et al. |
| 2006/0276749 A1 | 12/2006 | Selmon et al. |
| 2007/0208276 A1 | 9/2007 | Kornkven et al. |
| 2008/0114390 A1 | 5/2008 | Guinan |
| 2008/0125748 A1 | 5/2008 | Patel |
| 2008/0154172 A1 | 6/2008 | Mauch |
| 2008/0228169 A1 | 9/2008 | Schatz |
| 2009/0124899 A1 | 5/2009 | Jacobs et al. |
| 2010/0063534 A1 | 3/2010 | Kugler et al. |
| 2011/0144677 A1 | 6/2011 | Ward et al. |
| 2011/0196396 A1 | 8/2011 | Richter et al. |
| 2011/0276079 A1 | 11/2011 | Kugler et al. |
| 2012/0095485 A1 | 4/2012 | Cully et al. |
| 2012/0283571 A1 | 11/2012 | Nita |
| 2012/0283761 A1 | 11/2012 | Rosenthal et al. |
| 2012/0323251 A1 | 12/2012 | Kugler et al. |
| 2012/0323269 A1 | 12/2012 | Rottenberg et al. |
| 2013/0006167 A1 | 1/2013 | Alvarez |
| 2013/0006173 A1 | 1/2013 | Alvarez et al. |
| 2013/0006282 A1 | 1/2013 | Wilkinson |
| 2013/0072957 A1 | 3/2013 | Anderson |
| 2013/0103070 A1 | 4/2013 | Kugler et al. |
| 2013/0116622 A1 | 5/2013 | Takagi |
| 2013/0158519 A1 | 6/2013 | Boutilette et al. |
| 2013/0245430 A1 | 9/2013 | Selmon et al. |
| 2013/0296907 A1 | 11/2013 | Robinson et al. |
| 2013/0304108 A1 | 11/2013 | Weber et al. |
| 2013/0310868 A1 | 11/2013 | Kugler et al. |
| 2013/0317528 A1 | 11/2013 | Anderson et al. |

FOREIGN PATENT DOCUMENTS

| | | |
|---|---|---|
| EP | 2581105 | 4/2013 |
| WO | WO94/28961 | 12/1994 |
| WO | WO00/00104 | 1/2000 |
| WO | WO00/18323 | 4/2000 |
| WO | WO01/58360 | 8/2001 |
| WO | WO2007/058816 | 5/2007 |
| WO | WO2008/120209 | 10/2008 |
| WO | WO2009/144561 | 12/2009 |
| WO | WO2013003757 | 1/2013 |
| WO | WO2013164825 | 11/2013 |

(56) References Cited

OTHER PUBLICATIONS

Karkos et al. "Subintimal Recanalization of the Femoropopliteal Segment to Promote Healing of an Ulcerated Below-Knee Amputation Stump" J Endovasc Ther 2006;13:420-423.
Glasby et al. "Subintimal Angioplasty" Review, pp. 12-16, 2008.
Bolia, A. "Subintimial Angioplasty, the Way Forward" Acta Chir Belg, 2004, 104, 547-554.
Bolia A. "Subintimal Angioplasty, Tips and Technique: How Long Can You Go?".
Shin et al. "Limitations of the Outback LTD Re-Entry Device in Femoropopliteal Chroni Total Occlusions" Journal of Vascular Surgery, vol. 53, No. 5, pp. 1260-1264.

\* cited by examiner

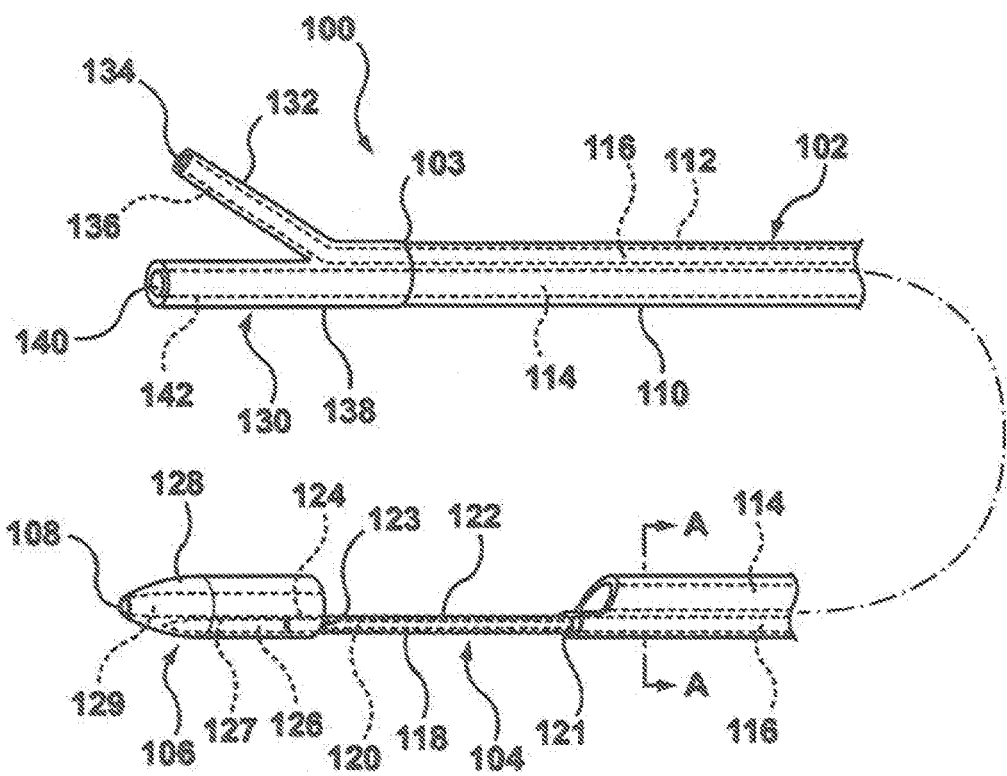
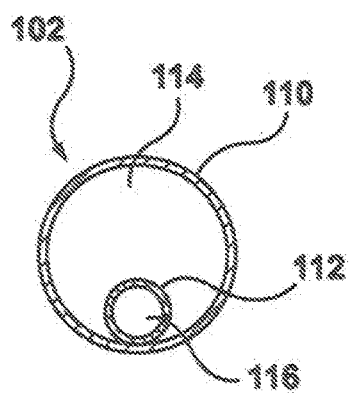 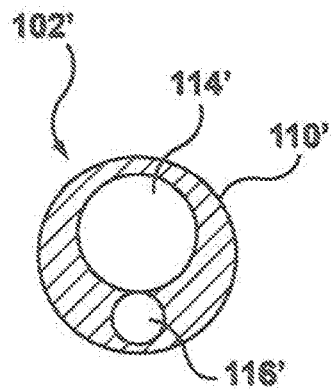

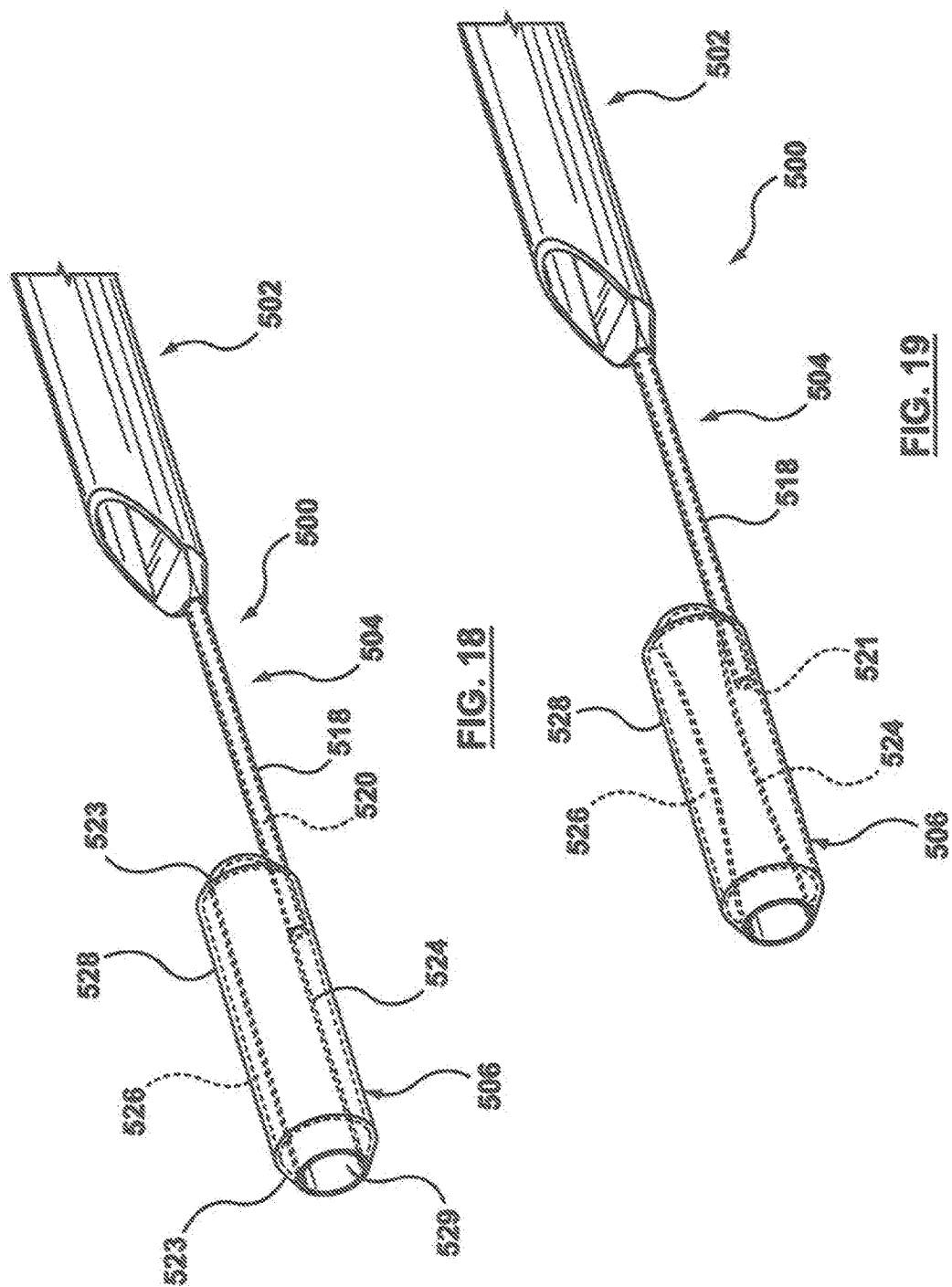

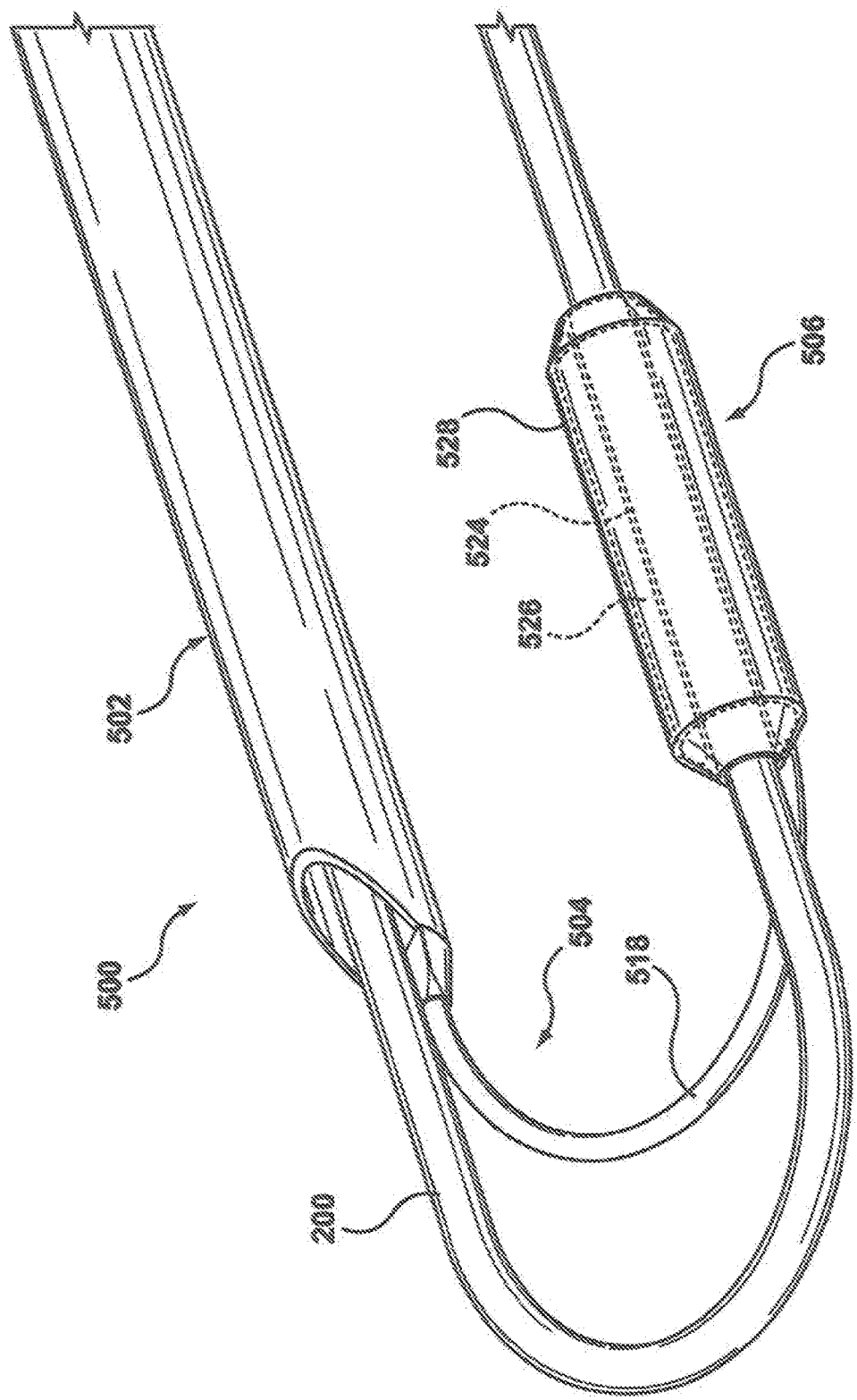

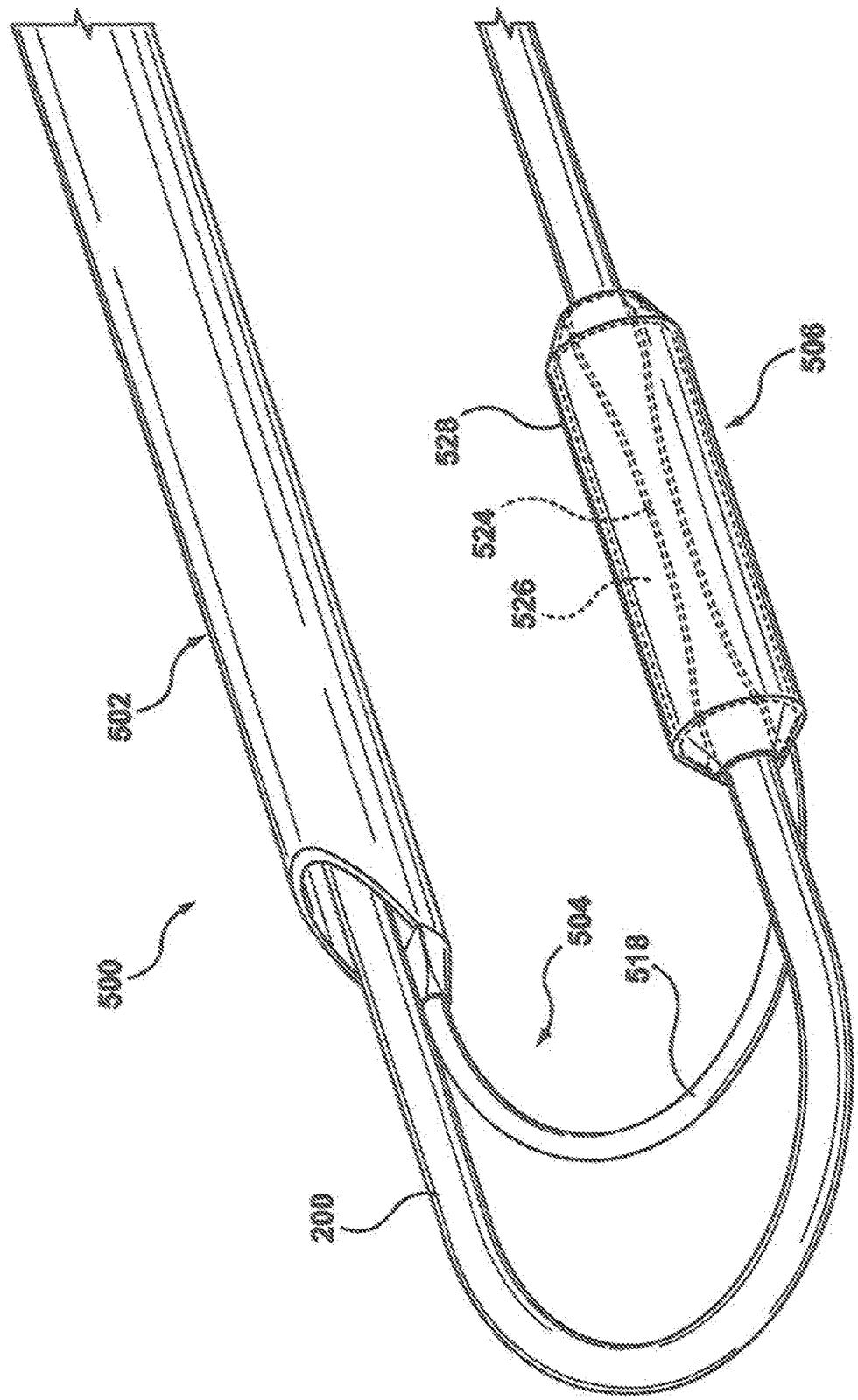

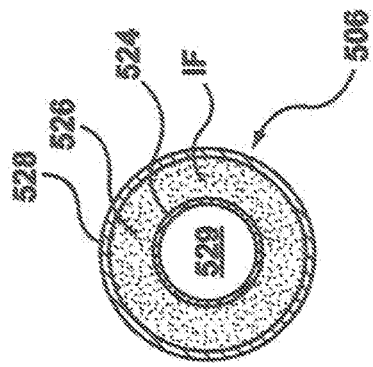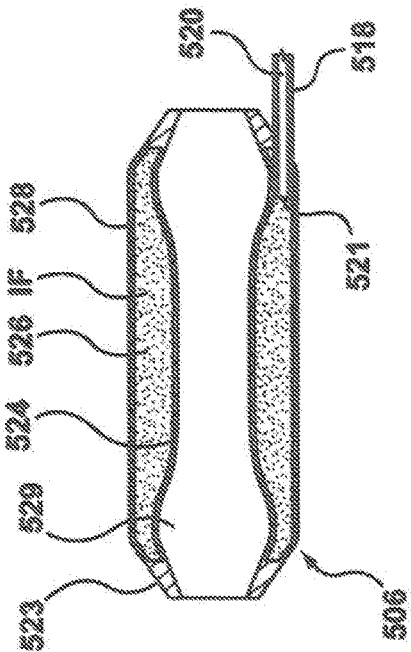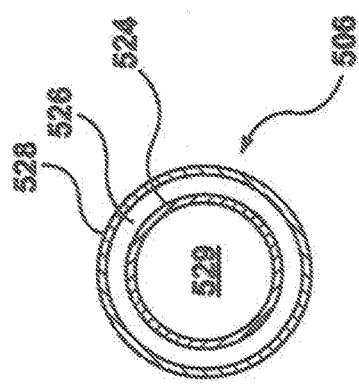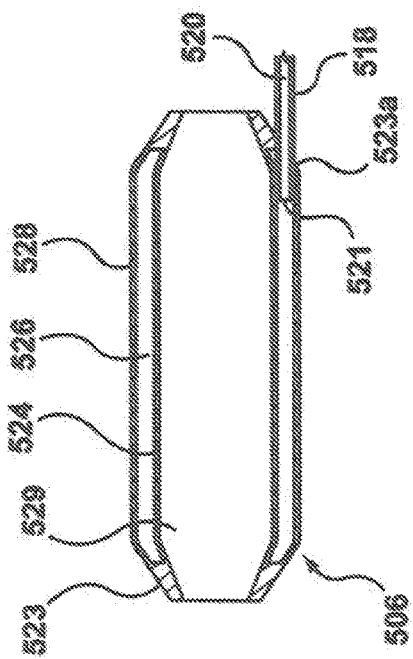

CATHETER SYSTEMS WITH A BLOCKING MECHANISM AND METHODS FOR BYPASSING AN OCCLUSION IN A BLOOD VESSEL

CROSS-REFERENCE TO RELATED APPLICATIONS

This application is a division of and claims priority to U.S. patent application Ser. No. 13/967,707 filed Aug. 15, 2013, now allowed, the contents of which are incorporated by reference herein in their entirety.

FIELD OF THE INVENTION

The invention relates generally to a catheter system and a method of using the catheter system in combination with a guidewire for subintimally bypassing a blockage in a blood vessel such as a chronic total occlusion and reentering the true lumen of the blood vessel beyond the blockage.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often, patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the interventionalist can successfully recanalize a CTO is the interventionalist's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

The most common site of a peripheral arterial CTO is the superficial femoral artery (SFA). Lesions in this area tend to be long (20-30 cm) and involve bulky, calcified plaque which also includes atheroma and organized thrombus. Dr. Bolia developed a revasculaturization procedure as described in *Recanalisation of femoro-popliteal occlusions: Improving success rate by subintimal recanalisation*, Clinic Radiol, 40:325, 1989, by exploiting the subintimal space where a guidewire enters the subintimal space between the intima and adventitia layers, is subsequently advanced to a point distal to the occlusion, and then maneuvered to re-enter or puncture the vessel layers to enter the true lumen of the vessel. Once the guide wire has traversed through the subintimal layer and re-enters the true lumen of the vessel at a point distal to the occlusion, percutaneous balloon angioplasty is performed to restore blood flow through subintimal recanalization.

Different devices have been developed for facilitating re-entry into the true lumen when using the subintimal approach of bypassing a CTO, such as the PIONEER® catheter system by Medtronic, Inc. Some of these re-entry devices may be complex and quite expensive. Accordingly, in many cases, the procedure is performed by forming a loop in the guidewire as it is advanced in the subintimal space, and then bluntly dissecting the intima using the loop to re-enter the true lumen distal of the occlusion. The loop formed by the guidewire is generally stiffer than a distal tip of the guidewire. Further, the loop is generally formed naturally by the forces of advancing the guidewire through the subintimal space acting on the flexible tip of the guidewire. However, rotation of the guidewire does not ensure that the loop is directed in the proper direction, i.e., towards the true lumen. Further, the loop may slide distally such that it is not successful in rupturing the intima layer to re-enter the true lumen. In some instances, the loop may be lost as the guidewire regains a straight shape during the procedure.

Accordingly, there is a need for an improved device and method to create a subintimal lumen from the true lumen of a vessel on a first side of an occlusion to the true lumen of the vessel on a second side of the occlusion.

BRIEF SUMMARY OF THE INVENTION

Embodiments hereof are directed to catheter used in conjunction with a subintimal reentry guidewire. The catheter includes a proximal portion, a distal portion, and an intermediate portion disposed between the proximal portion and the distal portion. The proximal portion includes a proximal guidewire lumen and a proximal inflation lumen disposed adjacent to the proximal guidewire lumen. The distal portion includes a distal guidewire lumen and a distal inflation lumen disposed adjacent the distal guidewire lumen. The intermediate portion is of a mono-lumen construction and includes an intermediate inflation lumen in fluid communication with the proximal inflation lumen and the distal inflation lumen. The intermediate portion is devoid of a guidewire lumen. The catheter further includes a blocking mechanism disposed in the distal portion of the catheter, the blocking mechanism being transformable between a non-blocking configuration in which a guidewire is free to translate through the distal guidewire lumen and a blocking configuration in which a guidewire disposed in the distal guidewire lumen is prevented from translating through the distal guidewire lumen. The blocking mechanism may be a distensible portion of a wall disposed between the distal inflation lumen and the distal guidewire lumen or a balloon in fluid communication with the distal inflation lumen and configured to expand into the distal guidewire lumen.

Embodiments hereof also include methods for reentering a blood vessel downstream or distal of an occlusion. In an embodiment of such a method, a guidewire is advanced in the true lumen of the blood vessel to a location proximal of the occlusion in the blood vessel. The guidewire is advanced into the subintimal space between layers of the blood vessel wall proximal to the occlusion and within the subintimal space such that a distal end of the guidewire is directed back proximally, thereby forming a loop in the guidewire in the subintimal space. A catheter is advanced over the guidewire. The catheter includes a proximal portion, a distal portion, and an intermediate portion disposed between the proximal portion and the distal portion. The proximal portion has a bi-lumen construction including a proximal guidewire lumen and a proximal inflation lumen disposed adjacent to the proximal guidewire lumen. The distal portion has a bi-lumen construction including a distal guidewire lumen and a distal inflation lumen disposed adjacent to the distal guidewire lumen. The intermediate portion has a mono-lumen construction including an intermediate inflation lumen in fluid communication with the distal inflation lumen and the proximal inflation lumen. The catheter is advanced over the guidewire such that the guidewire is disposed in the distal guidewire lumen and the proximal guidewire lumen and the catheter assumes the generally looped configuration of the guidewire. The method further includes activating a blocking mechanism to prevent a distal portion of the guidewire disposed in the distal guidewire lumen from translating within the distal guidewire lumen. After the blocking mechanism is activated, the guidewire is pushed such that the distal end of the guidewire does not advance while the loop formed in the guidewire expands distally. Further manipulation of the guidewire with the blocking mechanism activated causes an intermediate portion of the guidewire at the loop in the guidewire to perforate the wall of the vessel and reenter the true lumen distal of the occlusion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a schematic illustration of a catheter system for use with a reentry guidewire according to an embodiment hereof.

FIG. 2 is a sectional view taken along line A-A of FIG. 1.

FIG. 3 is another embodiment of a cross-sectional view taken along line A-A of FIG. 1.

FIG. 18 is a schematic illustration of a portion another embodiment of a catheter system for use with a reentry guidewire.

FIG. 19 is a schematic illustration of the catheter system of FIG. 18 with the blocking mechanism activated.

FIG. 20 is a schematic illustration the catheter system of FIG. 18 when in the position of the method of FIG. 9 with the blocking mechanism not activated.

FIG. 21 is a schematic illustration of the catheter system of FIG. 18 in the position of the method of FIG. 10 with the blocking mechanism activated.

FIG. 22 is a cross-sectional view of the distal portion of the catheter system of FIG. 18 with the blocking mechanism inactivated.

FIG. 23 is a cross-sectional view of the distal portion of the catheter system of FIG. 18 with the blocking mechanism activated.

FIG. 24 is a longitudinal cross-sectional view of the distal portion of the catheter system of FIG. 18 with the blocking mechanism inactivated.

FIG. 25 is a longitudinal cross-sectional view of the distal portion of the catheter system of FIG. 18 with the blocking mechanism activated.

DETAILED DESCRIPTION OF THE INVENTION

Figure 5A:
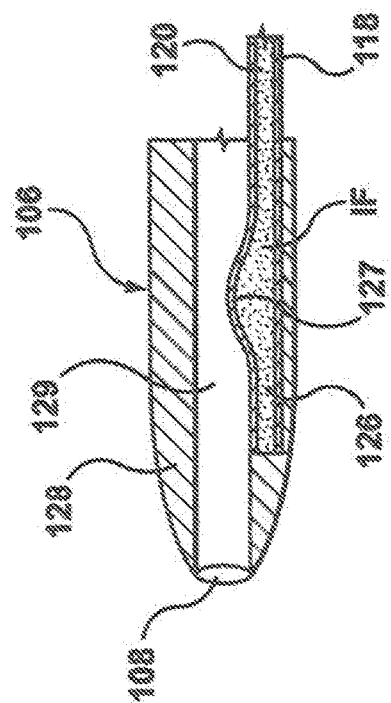
FIG. 5A is another embodiment of a longitudinal cross-sectional view of the distal portion of the catheter system of FIG. 1 with a blocking mechanism activated to prevent movement of a guidewire within the distal guidewire lumen.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to a system and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow if access is available from that direction. In other terms, the system and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Embodiments hereof relate to a system and method for re-entering the true lumen of a vessel after subintimally bypassing an occlusion in a blood vessel such as a chronic total occlusion (CTO) of an artery. As shown in FIG. 1, a catheter 100 according to an embodiment hereof includes a proximal portion 102, an intermediate portion 104, and a distal portion 106. Catheter 100 includes a proximal end 103 and a distal opening 108. Coupled to proximal end 103 of catheter 100 is a handle or luer 130, as will be described in more detail below.

Proximal portion 102 of catheter 100 is of a bi-lumen construction such that it includes a proximal first or guidewire lumen 114 and a proximal second or inflation lumen 116. As shown in FIG. 2, proximal portion 102 may include a proximal outer shaft 110 defining proximal first lumen 114 and a proximal inner shaft 112 defining proximal second lumen 116 disposed within proximal first lumen 114. Alternatively, as shown in FIG. 3, proximal portion 102' may include a proximal shaft 110' with a proximal first lumen 114' and a proximal second lumen 116' formed therein. Proximal portion 102 may have a length in the range of 70 to 150 cm. However, those skilled in the art would recognize that the length may be varied depending on the site being treated. Further, proximal guidewire lumen 114 may have a diameter to receive therein a guidewire with a diameter in the range of 0.014 inch to 0.035 inch. However, those skilled in the art would recognize that the size of guidewire lumen may be different if catheter 100 is configured to be used with a different size guidewire. Proximal inflation lumen 116 is sized such that an inflation fluid may pass therethrough to activate a blocking mechanism, as described in more detail below. In an embodiment, proximal inflation lumen may be 0.20 mm to 0.60 mm in internal diameter. As would be understood by those skilled in the art, other constructions or variations to proximal portion 102 may be utilized, provided that proximal portion includes at least two lumens disposed therethrough. Proximal portion 102 may be formed of traditional polymeric materials, e.g. polyamide. Alternatively, the proximal portion 102 may comprise a braided structure.

Intermediate portion 104 of catheter 100 is of a single or mono-lumen construction, as shown in FIG. 1. In particular, intermediate portion 104 includes an intermediate shaft 118 defining an intermediate second or inflation lumen 120. In the embodiment shown in FIG. 1, intermediate shaft 118 is a separate shaft joined to proximal portion 102 at bond 121 and to distal portion 106 at bond 123. Bonds 121 and 123 may be adhesive bonds, chemical bonds, fusion bonds, mechanical bonds, or other bonds known to those skilled in the art. Intermediate shaft 118 is coupled to proximal portion 102 such that intermediate inflation lumen 120 is in fluid communication with proximal inflation lumen 116. By having intermediate portion 104 as a separate intermediate shaft 118 coupled to proximal and distal portions 102, 106, characteristics of the different portions of catheter 100 may be varied by varying materials, construction, or other factors known to those skilled in the art. For example, and not by way of limitation, it is desirable for intermediate portion 104 to be highly flexible, as described in more detail below. Accordingly, intermediate shaft 118 may be made of highly flexible material or may be constructed such as to be highly flexible in bending, such as by having thin walls or including bellows 122, as shown in FIG. 1. It is also desirable for intermediate shaft 118 to exhibit good axial push (i.e., the push force acted on the proximal portion has to be transferred also to the intermediate and distal portions) and to be kink resistant such that the inflation lumen of intermediate shaft 518 remains patent during bending. Intermediate shaft 118 may have a coiled or braided structure (i.e. a metallic coil incorporated in one or more polymeric layers, or one or more wires incorporated in one or more polymeric layers). Although intermediate shaft 118 is shown as a separate shaft in the embodiment of FIG. 1, it would be understood by those skilled in the art that intermediate shaft 118 may be a continuation of proximal shaft 112. Intermediate portion 104 may have a length in the range of 10 mm to 30 mm. Intermediate lumen 120 preferably is approximately the same diameter as proximal inflation lumen 116. As would be understood by those skilled in the art, other constructions or variations to intermediate portion 104 may be utilized, including different sizes and materials.

Figure 5:
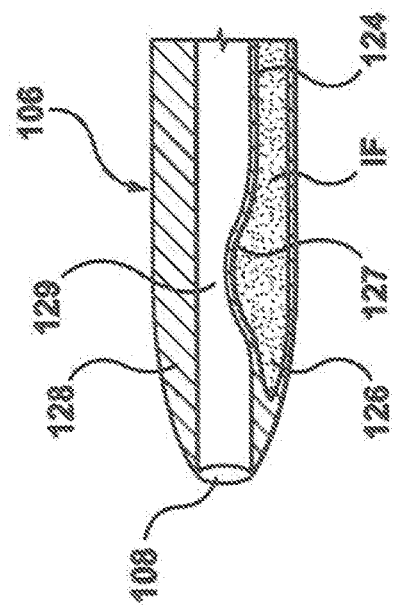
FIG. 5 is a side cross-sectional view of the distal portion of the catheter system of FIG. 1 with a blocking mechanism activated to prevent movement of a guidewire within the distal guidewire lumen.
Figure 4A:
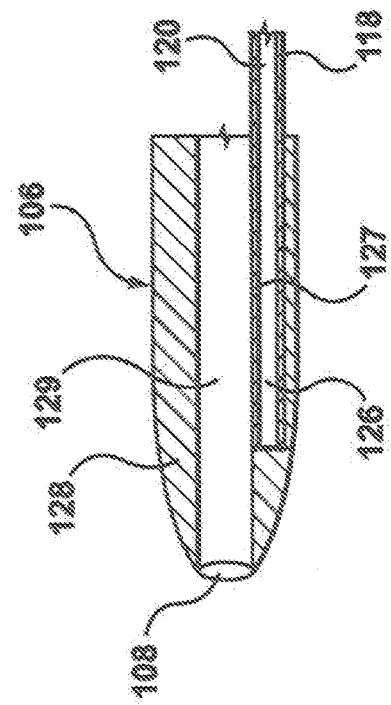
FIG. 4A is another embodiment of the longitudinal cross-sectional view of the distal portion of the catheter system of FIG. 1
Figure 4:
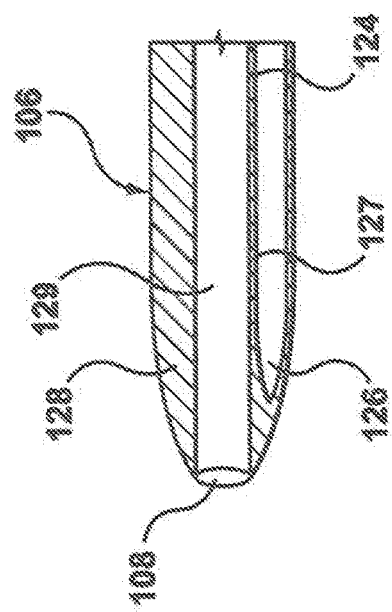
FIG. 4 is a longitudinal cross-sectional view of the distal portion of the catheter system of FIG. 1.

Referring to FIG. 1 and FIGS. 4-5, distal portion 106 of catheter 100 is of a bi-lumen construction such that it includes a distal first or guidewire lumen 129 and a distal second or inflation lumen 126. As shown in FIGS. 4-5, distal portion 102 may include a distal shaft 128 defining distal guidewire lumen 129 and distal inflation lumen 126, with a wall 124 separating distal guidewire lumen 129 and distal inflation lumen 126. As would be understood by those skilled in the art, other constructions for distal portion 106 may be utilized, such as a first shaft defining the distal guidewire lumen and a second shaft defining the distal inflation lumen. Alternatively, as shown in FIGS. 4A and 5A, intermediate shaft 118 may extend into distal inflation lumen 126 and terminate therein. With blocking mechanism 127 being a deformable wall of a distal portion of intermediate shaft 118. Distal portion 106 may have a length in the range of 10 mm to 20 mm. Distal guidewire lumen 129 is sized to accommodate the same size guidewire as proximal guidewire lumen 114. Distal inflation lumen 126 may be generally sized similarly to proximal inflation lumen 116 and intermediate lumen 120, although it is not necessary that they are of equal size. As would be understood by those skilled in the art, variations in sizes and construction may be utilized provided that the parts can perform the functions described below.

In the embodiment shown in FIGS. 1, 4, and 5, wall 124 includes a blocking mechanism 127 that can be activated to prevent a guidewire (not shown) disposed in distal guidewire lumen 129 from moving. In the embodiment of FIGS. 1, 4 and 5, blocking mechanism 127 is a distensible portion of wall 124. When an inflation fluid IF such as saline is injected into proximal inflation lumen 116, the inflation fluid IF fills proximal inflation lumen 116, intermediate inflation lumen 120, and distal inflation lumen 126, thereby causing blocking mechanism 127 to expand into distal guidewire lumen 129. Accordingly, blocking mechanism 127 includes an inactivated, delivery, or non-blocking configuration where blocking mechanism does not prevent movement of the guidewire within distal guidewire lumen 129, and an activated or blocking configuration wherein blocking mechanism 127 prevents movement of the guidewire within distal guidewire lumen 129, as explained in more detail below. Although blocking mechanism 127 is described in the present embodiment as a distensible portion of wall 124, blocking mechanism 127 could be other mechanisms to prevent a guidewire disposed within distal guidewire lumen 129 from moving. For example, and not by way of limitation, other blocking mechanisms may include a balloon in fluid communication with distal inflation lumen 126 or a mechanical arm coupled to a wire or other mechanical mechanism extending proximally through distal second lumen 126 and proximal second lumen 116. Such a wire or mechanical mechanism can also extend through intermediate lumen 120 or intermediate lumen 120 may be eliminated such that the wire or mechanical mechanism forms intermediate portion 104 of catheter 100. Such a mechanical arm may be activated by the wire or mechanical mechanism hold a guidewire disposed within distal guidewire lumen 129.

Coupled to a proximal portion of proximal portion 102 is a handle or hub 130, such as a Tuohy-Burst luer. In the embodiment shown, hub 130 includes a first arm or branch 132 and a second arm or branch 138. First branch 132 includes a first proximal opening 134 leading to a first lumen 136. First lumen 136 is in fluid communication with proximal inflation lumen 116. Second branch 138 includes a second proximal opening 140 and a second lumen 142 in communication with proximal guidewire lumen 114. Hub 130 may be overmolded or otherwise coupled to proximal portion 102. Hub 130 may also include other features known to those skilled in the art, such as a strain relief member, hemostatic valves, etc.

Optionally, catheter 100 may incorporate one or more radiopaque markers (not shown) that are strategically located on proximal portion 102, intermediate portion 104, and/or distal portion 106 to be imageable by an imaging apparatus for aiding a clinician in delivery of catheter 100 a correct rotational position at the treatment site. Preferably, catheter 100 comprises only one radiopaque marker that is positioned at the distal end of proximal portion 102. Alternatively, catheter 100 comprises one radiopaque marker at the distal end of proximal portion 102 and one radiopaque marker at the distal portion 106.

FIGS. 18-25 show another embodiment of a catheter 500 to be used with a re-entry guidewire for re-entering the true lumen of a vessel after subintimally bypassing an occlusion in a blood vessel such as a chronic total occlusion (CTO) of an artery. As shown in FIG. 18, catheter 500 includes a proximal portion 502, an intermediate portion 504, and a distal portion 506. Proximal portion 502 is of a bi-lumen construction such as shown with respect to proximal portion 104 of catheter 100 in FIGS. 1-3. Further, other features of proximal areas of catheter 500 can be as described above with respect to FIGS. 1-3, such as a hub or luer. Accordingly, such descriptions will not be repeated in this embodiment and the descriptions above with respect to FIGS. 1-3 are incorporated into the present embodiment.

Intermediate portion 504 of catheter 500 is of a single or mono-lumen construction, as shown in FIGS. 18-19. In particular, intermediate portion 504 includes an intermediate shaft 518 defining an intermediate second or inflation lumen 520. In the embodiment shown in FIGS. 18-21, intermediate shaft 518 is a separate shaft which may be joined to proximal portion 502 at a bond, as described above with respect to FIG. 1, or may be a separate shaft that extends through a lumen in proximal portion 502. Those skilled in the art would recognize that other configurations for how intermediate shaft 518 connects or interacts with proximal portion 502 may be used provided that inflation fluid injected into the inflation lumen of proximal portion 502 is in fluid communication with intermediate inflation lumen 520 defined by intermediate shaft 518. As described above, it is desirable for intermediate portion 504 to be highly flexible, particularly during bending, as described in more detail below with respect to the method described herein. It is also desirable for intermediate shaft 518 to exhibit good axial push (i.e., the push force acted on the proximal portion has to be transferred also to the intermediate and distal portions) and to be kink resistant such that the inflation lumen of intermediate shaft 518 remains patent during bending. Intermediate shaft 518 may have a coiled or braided structure (i.e. a metallic coil incorporated in one or more polymeric layers, or one or more wires incorporated in one or more polymeric layers). Intermediate portion 504 may have a length in the range of 10 mm to 30 mm. Intermediate lumen 520 preferably is approximately the same diameter as the proximal inflation lumen. As would be understood by those skilled in the art, other constructions or variations to intermediate portion 504 may be utilized, including different sizes and materials.

Referring to FIGS. 18-25, distal portion 506 of catheter 500 includes a distal inner or guidewire shaft 524 and a distal outer tube or membrane 528. Distal guidewire shaft 524 defines a distal guidewire lumen 529. Distal outer membrane 528 is bonded or otherwise attached to distal guidewire shaft 524 at connections 523 such that a cavity or chamber or annular lumen 526 is defined between an outer surface of distal guidewire shaft 524 and an inner surface of distal outer membrane 528. Connections 523 may be via heat bonding, fusion, mechanical connection, or other connections known to those skilled in the art. Further, instead of connections 523, distal outer membrane 528 may be coupled to distal guidewire shaft 524 by overmolding or other techniques known to those skilled in the art. Distal outer membrane 528 is also coupled to a distal portion of intermediate shaft 518, as shown in FIGS. 24 and 25 at connection 523a. Distal guidewire shaft 524 may be formed of materials generally used for guidewire shafts or distal tips of catheters. Distal outer membrane 528 may be formed of materials such as, but not limited to, polymeric materials commonly used in catheters, such as PEBA, polyurethane, and polyimide, and other materials commonly. Those skilled in the art would recognize that other materials can be used. The material characteristics of distal outer membrane 528 as compared to distal guidewire shaft 524 are selected such that upon injection of inflation fluid IF in annular lumen 526, the wall of distal guidewire shaft 524 is deformed to contract the diameter of distal guidewire lumen 529, as shown in FIGS. 19, 21, 23, 25. Those skilled in the art would also recognize that the materials for distal outer membrane 528 and distal guidewire shaft 524 may be the same, but that other characteristics such as thickness may result in distal guidewire shaft 524 deforming upon injection of inflation fluid IF in inflation lumen 526. In this embodiment, as shown in FIGS. 19, 21, 23, and 25 the wall of distal guidewire shaft 524 is compressed around its entire cross-sectional circumference due to annular inflation lumen 526 completely surrounding distal guidewire shaft 524. Thus, the compression of distal guidewire shaft 524 is uniform, homogeneous and very effective (the blockage force and blockage action are balanced and occurs on the whole external circumferential surface of distal guidewire shaft 524).

Figure 6:
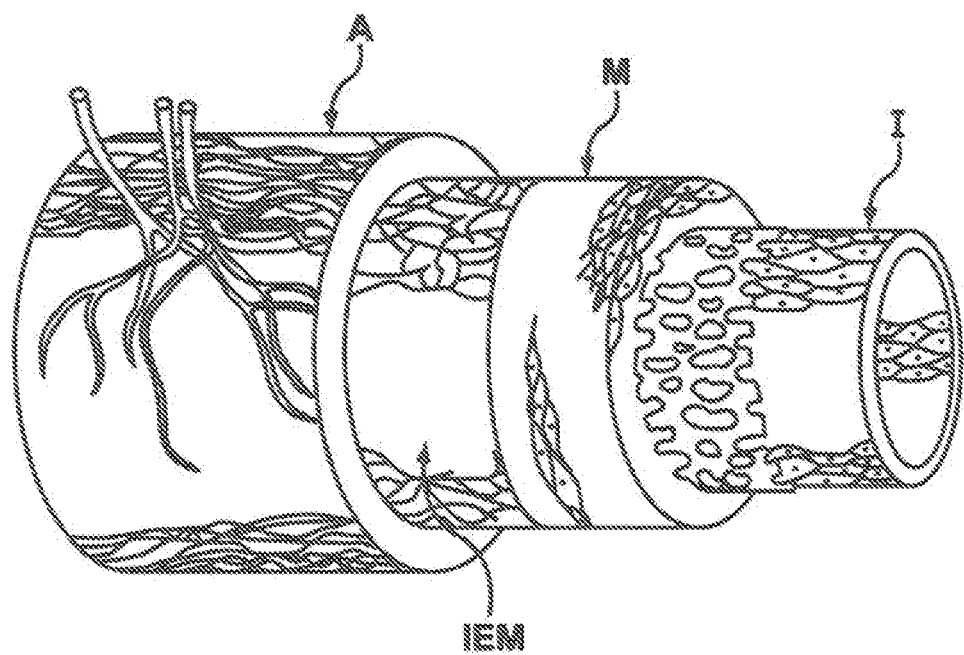
FIG. 6 is a diagram of an artery showing the three layers of tissue that comprise the artery wall.

FIG. 6 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood.

FIGS. 7-17 illustrate a prophetic method of using the above-described catheter 100 or catheter 500 to support a subintimal reentry guidewire 200 to bypass a chronic total occlusion O according to an embodiment hereof. FIGS. 7-17 are shown with catheter 100, but the steps shown and described with respect to FIGS. 7-17 apply equally to catheter 500. Subintimal reentry guidewire 200 can be any subintimal reentry guidewire known to those skilled in the art, or future subintimal reentry guidewires developed, as the present invention is directed to catheter 100 and its use with the subintimal reentry guidewire. FIGS. 7-12 illustrate only the intima I and adventia A layers of the vessel V for convenience of the illustration. Accordingly, as shown in FIGS. 7-17 and described in more detail below, catheter 100 and subintimal reentry guidewire 200 are advanced between the intima I and adventia A layers of the vessel V, typically between the intima I and the media M. Catheter 100 and subintimal reentry guidewire 200 may be used as part of a system for creating a subintimal reentry conduit within a wall of a blood vessel V, such as an artery located below the knee of a patient, to allow blood flow around the occlusion. Although described in relation to bypassing a chronic total occlusion O, it should be understood that the methods and apparatus described herein may be used for bypassing any tight stenoses in arteries or other anatomical conduits and are not limited to total occlusions. Typically, a guiding catheter and/or an introducer sheath (not shown) are first inserted percutaneously into a femoral artery of a patient. Subintimal reentry guidewire 200 is inserted into the guiding catheter and maneuvered through the vasculature to a treatment site, which in this instance is shown as a total occlusion O within a lumen 301 of blood vessel V.

Figure 7:
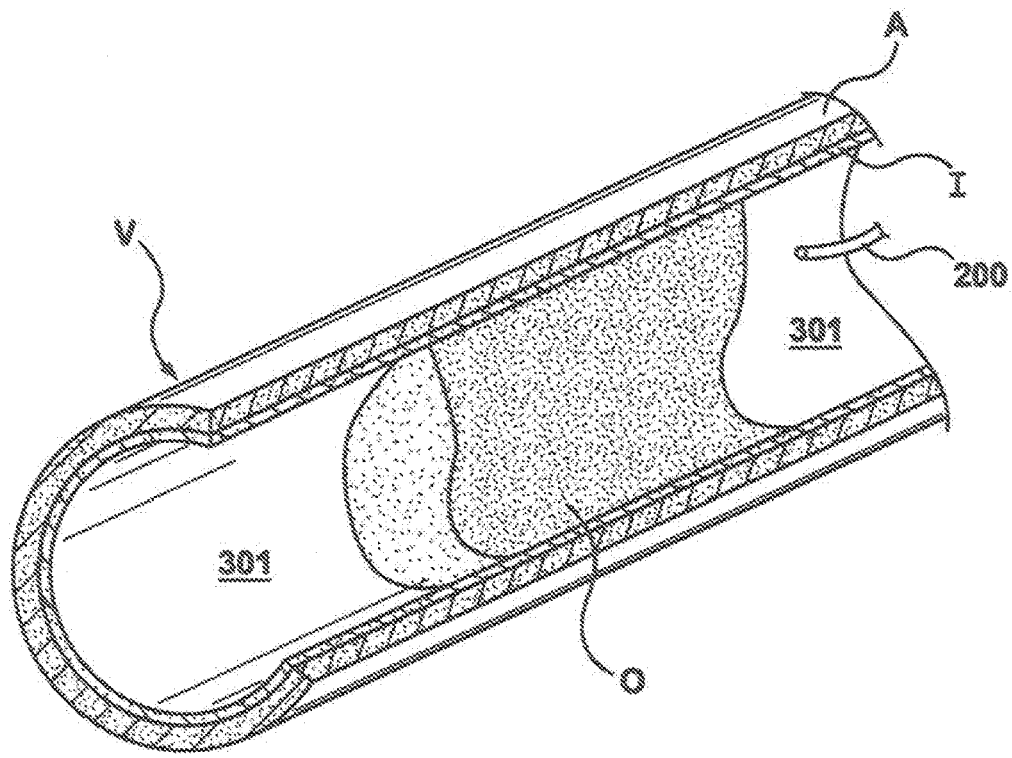
FIGS. 7-17 illustrate the steps of utilizing the catheter system of FIG. 1 with a subintimal reentry guidewire to bypass a chronic total occlusion according to an embodiment hereof.
Figure 8:
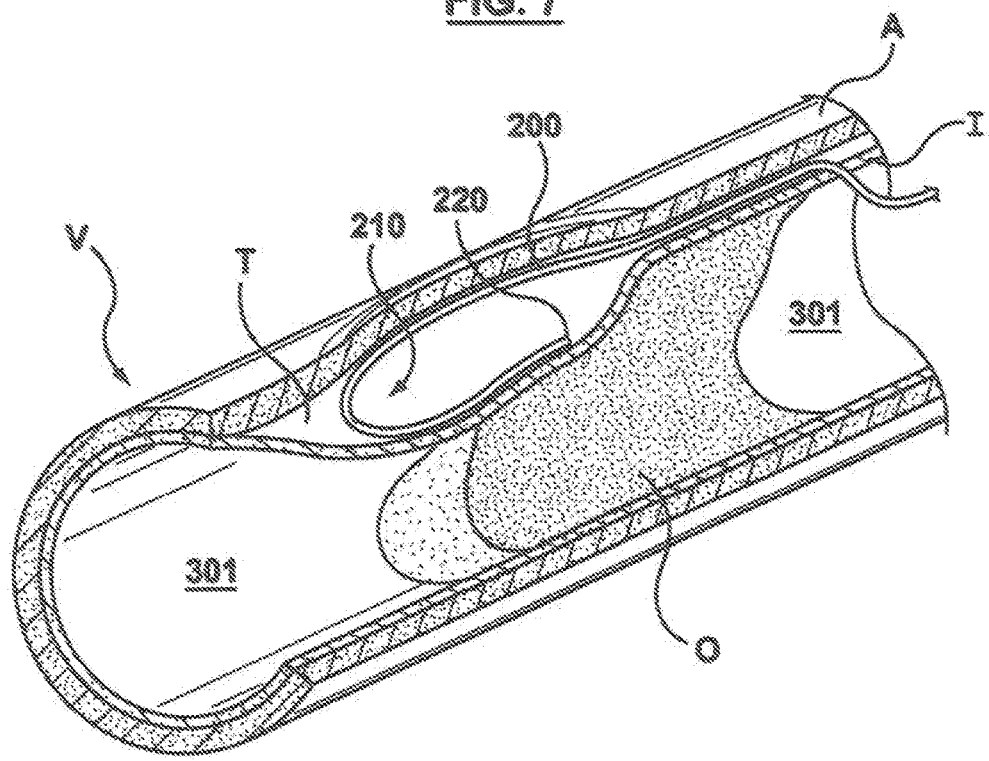

Referring to FIGS. 7-8, in accordance with techniques known in the field of interventional cardiology and/or interventional radiology, subintimal reentry guidewire 200 is transluminally advanced through lumen 301 of blood vessel V to a position upstream of occlusion O. Subintimal reentry guidewire 200 pierces the intima I and is advanced distally to create a subintimal tract T by locally dissecting or delaminating intima I from media M. In order to pierce the intima I, a clinician may manipulate the distal end of the subintimal reentry guidewire 200 by prolapsing or bending-over the distal end of subintimal reentry guidewire 200 and thereafter may use the stiffer arc of the prolapsed distal end to pierce into the intima I to advance subintimal reentry guidewire 200 there through. The piercing of the intima I is aided by the fact that typically blood vessel V is diseased, which in some instances makes the intima I prone to piercing. Subintimal reentry guidewire 200 is advanced within the subintimal tract T from a proximal side of occlusion O distally. As subintimal reentry guidewire 200 is advanced distally within the subintimal tract, forces acting against guidewire 200 as the clinician pushes guidewire 200 cause a tip 220 of guidewire 200 to bend back proximally to form a loop 210, as shown in FIG. 8.

Figure 9:
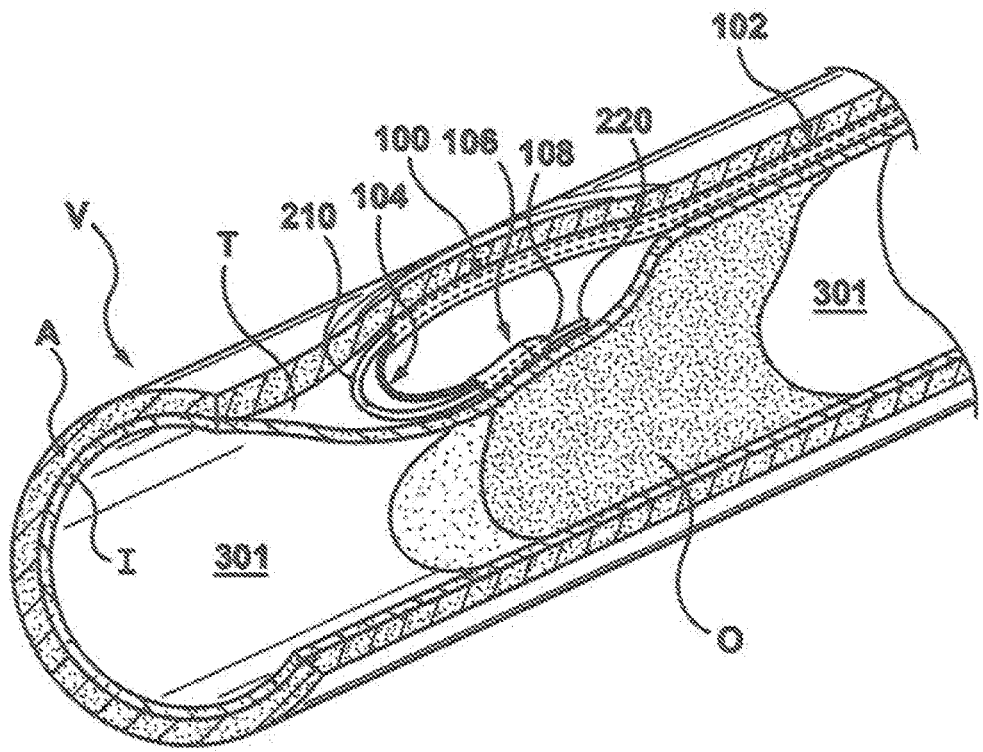

With the formation of loop 210 confirmed such as by imaging, guidewire 200 is backloaded into catheter 100 by inserting a proximal end (not shown) of guidewire 200 into distal opening 108 of catheter 100, as known in the art. Catheter 100 is advanced distally over guidewire 200, conforming to the shape of guidewire 200, including loop 210, as illustrated schematically in FIG. 9. This configuration is also shown schematically in FIG. 21 with respect to catheter 500, without the vessel V or occlusion O depicted. As can be seen in FIG. 9, it is desirable for intermediate portion 104 of catheter 100 to be highly flexible in bending in order to conform to the looped shape of guidewire 200 without kinking and without causing guidewire 200 to lose its looped shape. In other words, intermediate portion 104 of catheter 100, and catheter 100 generally, should be sufficiently flexible such that when advancing catheter 100 over guidewire 200, catheter 100 does not straighten guidewire 200.

Figure 10:
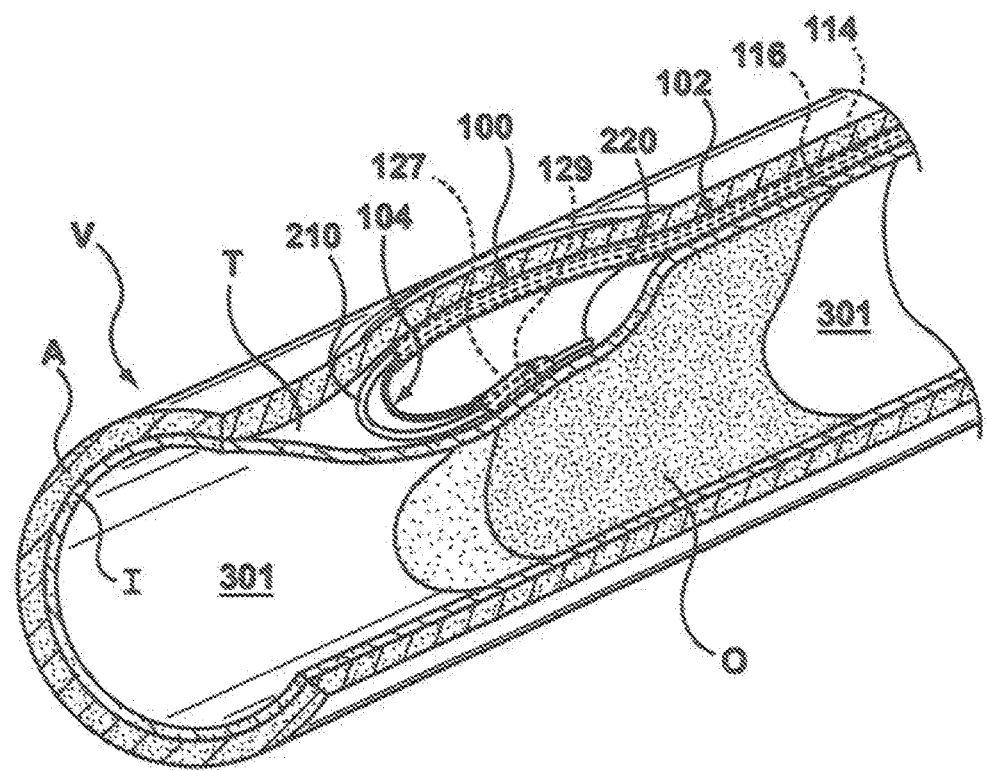

After catheter 100 is advanced over guidewire 200 into the position shown in FIG. 9, blocking mechanism 127 is activated. In the embodiment shown, blocking mechanism 127 is activated by injecting an inflation fluid into first lumen 136 of first branch 132 of hub 130 described above. The inflation fluid advances through first lumen 136 into proximal inflation lumen 116, intermediate inflation lumen 120, and into distal inflation lumen 126. As distal inflation lumen 126 is filled with the inflation fluid and pressure builds therein, wall 124 forming blocking mechanism 127 is distended or expanded into distal guidewire lumen 129, as shown in FIGS. 5 and 10. Although FIG. 5 does not show guidewire 200 disposed within distal guidewire lumen 129, FIG. 10 does show guidewire 200 shown in distal guidewire lumen 129. With guidewire 200 disposed in distal guidewire lumen 129, expansion of blocking mechanism 127 into distal guidewire lumen 129 applies pressure to guidewire 200 between blocking mechanism and a portion of shaft 128 opposite blocking mechanism 127 to resist forces that would tend to move guidewire 200 within distal guidewire lumen 129. Similarly, FIG. 21 shows catheter 500 generally in this position with inflation fluid filling annular lumen 526 such that the walls of distal guidewire shaft 524 compress radially around the guidewire disposed in distal guidewire lumen 529.

Figure 11:
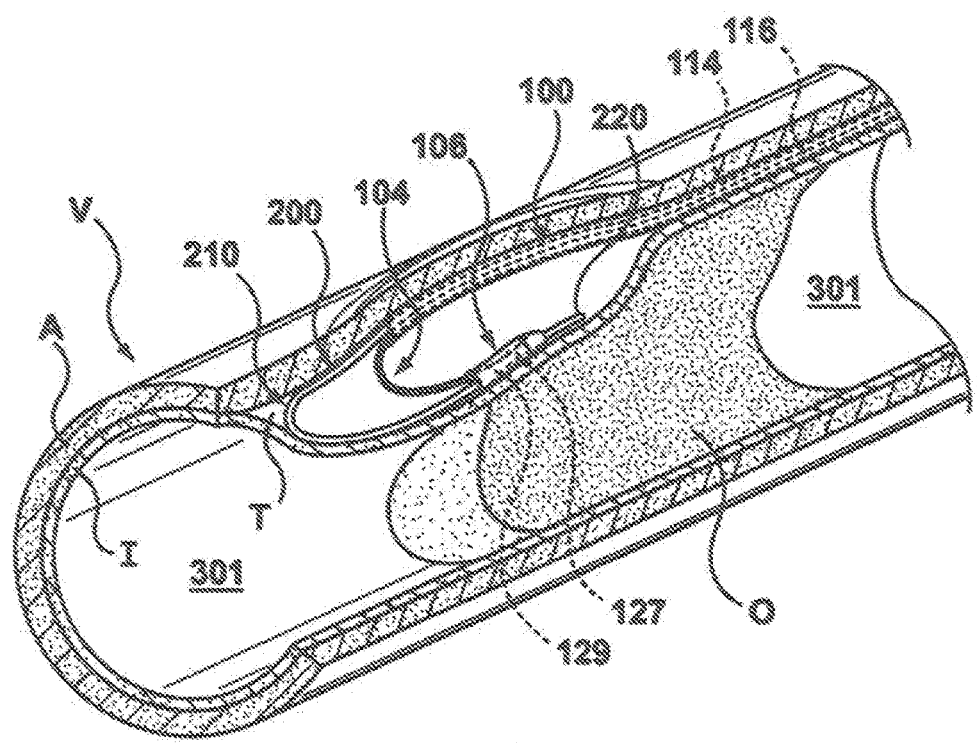
Figure 12:
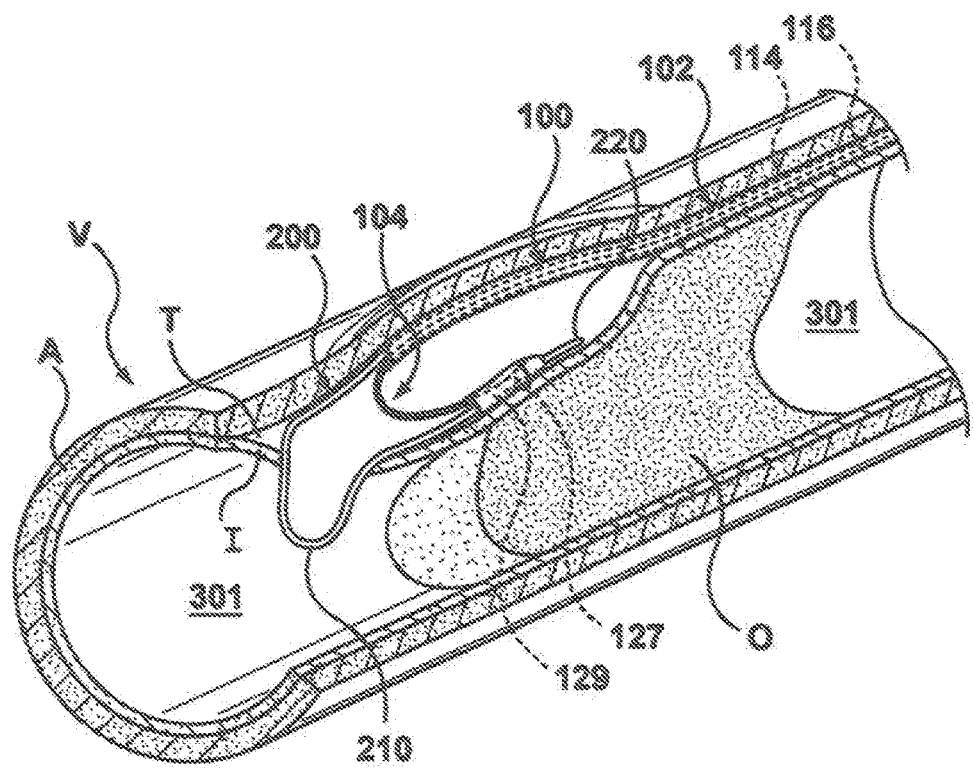

With blocking mechanism 127 activated, the clinician can push, twist, and rotate guidewire 200 with improved control because such actions are done against a force of blocking mechanism 127 resisting advancement of guidewire 200 in the direction towards distal tip 220 of guidewire 200. Accordingly, loop 210 of guidewire can be properly oriented towards intima I distal of the occlusion O. Further, as guidewire 200 is pushed, loop 210 expands in the distal direction, as shown in FIG. 11. With blocking mechanism 127 activated, loop 210 of guidewire 200 may be suitably controlled by the clinician and used for perforating the intima I and entering the true lumen 301 downstream of the occlusion O, as shown in FIG. 12.

Figure 13:
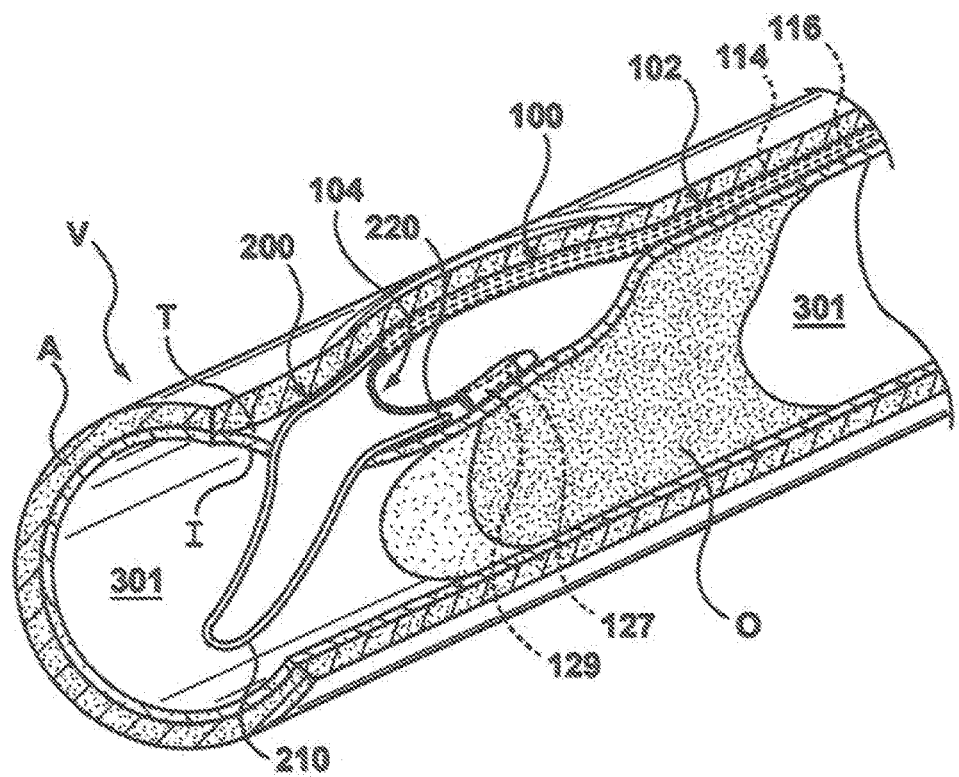
Figure 14:
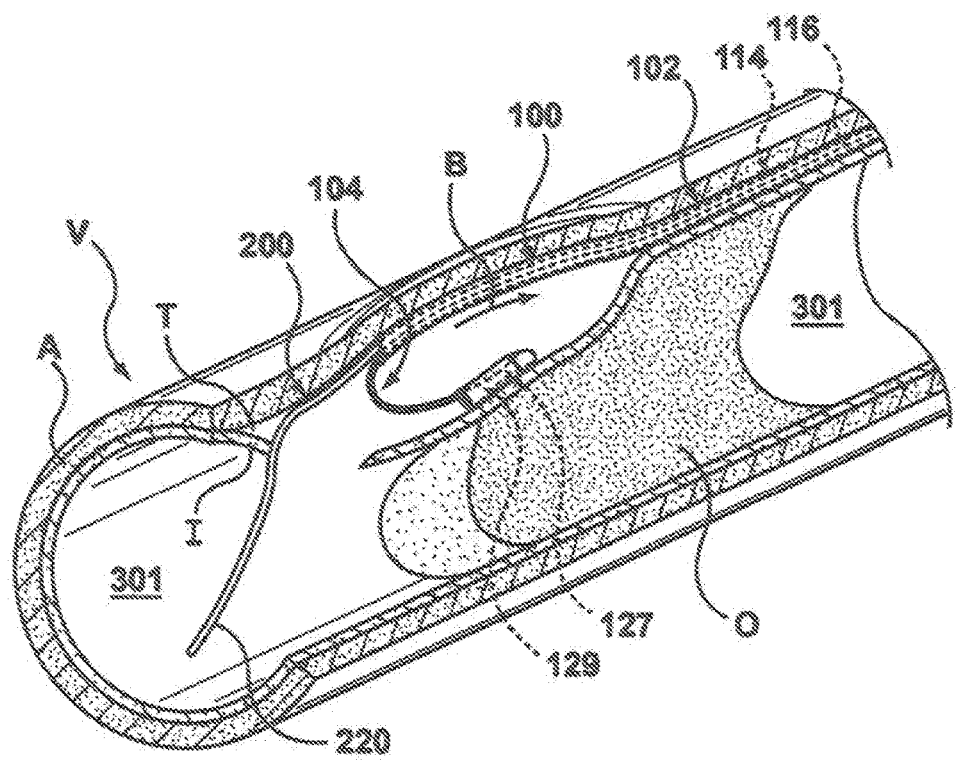

Once loop 210 perforates the intima I and enters the true lumen 301 distal of the occlusion O, blocking mechanism 127 may be deactivated by draining the inflation fluid from distal inflation lumen 126. Methods and devices for draining inflation fluid from an inflation lumen are known in the art. The operator can then push on guidewire 200, which causes loop 210 to continue to advance in true lumen 301 while also pulling distal tip 220 through distal portion 106 of catheter 100 such that distal tip is freed from distal portion 106, as shown in FIG. 13. Continued manipulation of guidewire 200 results in distal tip 220 entering the true lumen 301 distal of the occlusion O through the perforation created by the loop 210, and eventually the loop 210 being straightened such that guidewire is generally in the configuration shown in FIG. 14. Catheter 100 can then be retracted proximally as indicated by arrow B in FIG. 14, and removed from the body. Although FIG. 14 shows catheter 100 being retracted after loop 210 of guidewire 200 has been straightened, those skilled in the art would recognize that catheter 100 may be retracted without guidewire 200 being straightened. Instead, catheter 100 may be retracted once guidewire 200 has entered the true lumen and blocking mechanism 127 has been deactivated to release the guidewire 200.

Figure 15:
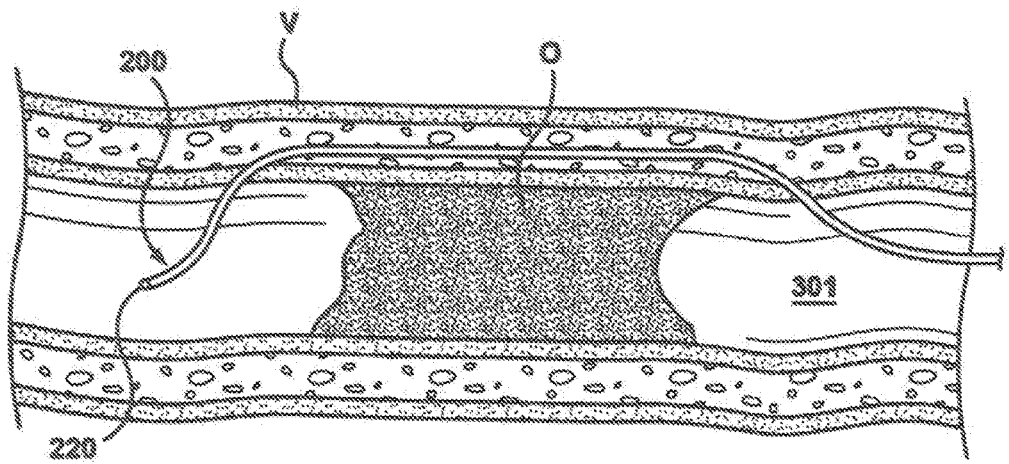

With catheter 100 proximally retracted and removed from the patient, subintimal reentry guidewire 200 extends in true lumen 301 proximal to occlusion O, through the subintimal tract T, and back into true lumen 301 distal to occlusion O such that occlusion O may now be successfully crossed via the subintimal conduit thus created, as shown in FIG. 15.

Figure 16:
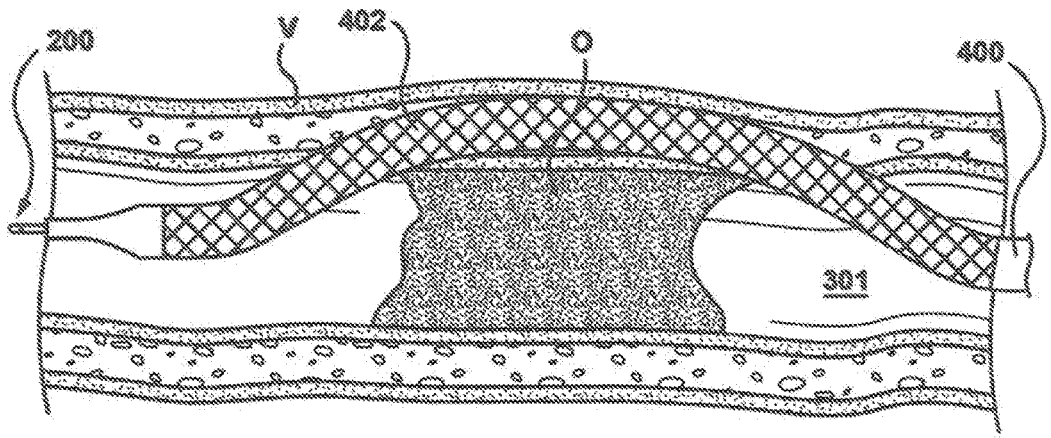
Figure 17:
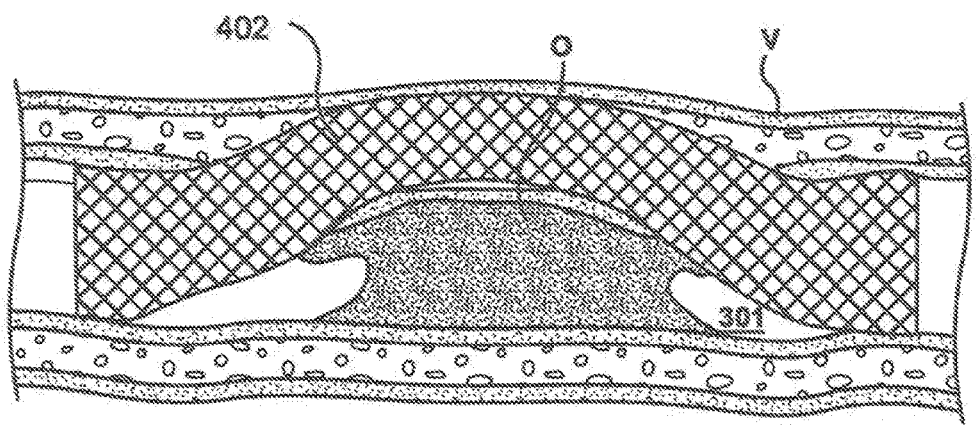

Optionally, a covered or uncovered stent may be placed within the subintimal reentry conduit to facilitate flow from the lumen of the vessel upstream of occlusion O, through the subintimal tract T and back into the lumen of the vessel downstream of occlusion O. For example, FIG. 16 shows a distal end of a catheter 400 having a stent 402 mounted thereon being advanced over guidewire 200 to a position where a distal end of the radially collapsed stent 402 is in true lumen 301 of vessel V downstream of occlusion O, a proximal end of stent 402 is in true lumen 301 of vessel V upstream of occlusion O, and a mid-portion of stent 402 extends through the subintimal conduit. Stent 402 may then be deployed by either self-expansion or balloon inflation within the subintimal conduit to dilate the subintimal conduit and compress the adjacent occlusion O. Stent 402 provides a scaffold which maintains the subintimal conduit in an open condition capable of carrying blood downstream of occlusion O. Thereafter, guidewire 200 and catheter 400 may be removed from the patient, leaving stent 402 in an expanded configuration and creating a radially supported, subintimal blood flow channel around occlusion O as seen in FIG. 17. In some cases, it may be desirable to enlarge the diameter of the subintimal tract before or instead of advancing stent catheter 400 into and through it. Such enlargement of the subintimal tract may be accomplished by passing a balloon catheter over guidewire 200 and inflating the balloon to dilate the tract, or may be any other suitable tract enlarging, dilating or de-bulking instrument that may be passed over guidewire 200.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of bypassing an occlusion in a true lumen of a blood vessel, the method comprising the steps of:
    advancing a guidewire in the true lumen of the blood vessel to a location proximal of the occlusion in the blood vessel, into a subintimal space between layers of the blood vessel wall proximal to the occlusion, and within the subintimal space such that a distal end of the guidewire is directed back proximally, thereby forming a loop in the guidewire in the subintimal space;
    advancing a catheter over the guidewire, the catheter including,
        a proximal portion having a bi-lumen construction including a proximal guidewire lumen and proximal inflation lumen disposed adjacent to the proximal guidewire lumen;
        a distal portion having a bi-lumen construction including a distal guidewire lumen and a distal inflation lumen disposed adjacent to the distal guidewire lumen; and
        an intermediate portion disposed between the proximal portion and the distal portion and having a mono-lumen construction including an intermediate inflation lumen in fluid communication with the distal inflation lumen and the proximal inflation lumen, wherein the catheter is advanced over the guidewire such that the guidewire is disposed in the distal guidewire lumen and the proximal guidewire lumen and the catheter assumes a generally looped configuration confirming to the loop of the guidewire,
    preventing a distal portion of the guidewire disposed in the distal guidewire lumen from translating within the distal guidewire lumen; and
    pushing the guidewire such that the distal end of the guidewire does not advance and the loop formed in the guidewire advances distally.

2. The method of claim 1, further comprising the step of manipulating the guidewire such that an intermediate portion of the guidewire at the loop in the guidewire perforates the wall of the vessel and enters the true lumen distal of the occlusion.

3. The method of claim 2, further comprising the steps of:
    after the guidewire enters the true lumen distal of the occlusion, deactivating the blocking mechanism such that the guidewire is free to move within the distal guidewire lumen;
    distally advancing the guidewire such that the distal end of the guidewire exits the distal portion of the catheter and enters the true lumen distal of the occlusion; and
    proximally retracting the catheter and withdrawing the catheter from the patient.

4. The method of claim 3, further comprising the steps of:
    tracking a stent delivery catheter with a stent mounted thereon over the guidewire until the stent extends from the true lumen proximal of the occlusion through the subintimal space and into the true lumen distal of the occlusion;
    deploying and radially expanding the stent; and
    removing the stent delivery catheter and leaving the stent in place, such that fluid may flow from the true lumen of the blood vessel on one side of the occlusion through the stent and into the true lumen of the blood vessel on the other side of the occlusion.

5. The method of claim 1, wherein the step of preventing the distal portion of the guidewire from translating comprises activating a blocking mechanism to reduce a diameter of the distal guidewire lumen.

6. The method of claim 5, wherein a distal end of the distal inflation lumen is closed, and wherein the blocking mechanism comprises a flexible wall defining the distal inflation lumen.

7. The method of claim 6, wherein the step of preventing the distal portion of the guidewire from translating comprises injecting an inflation fluid into the distal inflation lumen such that the flexible wall expands to impinge on the guidewire in the distal guidewire lumen.

8. The method of claim 5, wherein the blocking mechanism comprises a balloon disposed at a distal portion of the distal inflation lumen.

9. The method of claim 8, wherein the step of preventing the distal portion of the guidewire from translating comprises injecting an inflation fluid into the distal inflation lumen such that the balloon expands to impinge on the guidewire in the distal guidewire lumen.

10. The method of claim 5, wherein the distal portion comprises a distal guidewire shaft defining the distal guidewire lumen and the blocking mechanism comprises a distal outer tube surrounding the distal guidewire shaft such that the distal inflation lumen is an annular inflation lumen defined between an outer surface of the distal guidewire shaft and an inner surface of the distal outer tube.

11. The method of claim 10, wherein the step of preventing the distal portion of the guidewire from translating comprises injecting an inflation fluid into the distal inflation lumen such that the distal guidewire shaft compresses radially to reduce the diameter of the distal guidewire lumen.

12. The method of claim 1, wherein the blood vessel is an artery located in the leg of a human subject.

13. The method of claim 1, wherein the blood vessel is a coronary artery.

14. The method of claim 1, wherein the occlusion is a chronic total occlusion located in an artery.

15. A method of bypassing an occlusion in a true lumen of a blood vessel, the method comprising the steps of:
    advancing a guidewire in the true lumen of the blood vessel to a location proximal of the occlusion in the blood vessel, into a subintimal space between layers of the blood vessel wall proximal to the occlusion, and within the subintimal space such that a distal end of the guidewire is directed back proximally, thereby forming a loop in the guidewire in the subintimal space;
    advancing a catheter over the guidewire, the catheter including,
        a proximal portion including a first proximal lumen,
        a distal portion having a bi-lumen construction including a first distal lumen and a second distal lumen, and
        an intermediate portion disposed between the proximal portion and the distal portion and having a mono-lumen construction including an intermediate lumen in communication with the first distal lumen and the first proximal lumen,
    wherein the catheter is advanced over the guidewire such that the guidewire is disposed in the second distal lumen and adjacent to the first proximal lumen and the catheter assumes a generally looped configuration conforming to the loop of the guidewire;
    preventing a distal portion of the guidewire disposed in the second distal lumen from translating within the second distal lumen; and
    pushing the guidewire such that the distal end of the guidewire does not advance and the loop formed in the guidewire advances distally.

16. The method of claim 15, further comprising the step of manipulating the guidewire such that an intermediate portion of the guidewire at the loop in the guidewire perforates the wall of the vessel and enters the true lumen distal of the occlusion.

17. The method of claim 16, further comprising the steps of:
    after the guidewire enters the true lumen distal of the occlusion, deactivating the blocking mechanism such that the guidewire is free to move within the second distal lumen;
    distally advancing the guidewire such that the distal end of the guidewire exits the distal portion of the catheter and enters the true lumen distal of the occlusion; and
    proximally retracting the catheter and withdrawing the catheter from the patient.

18. The method of claim 15, wherein the step of preventing the distal portion of the guidewire from translating comprises activating a blocking mechanism to reduce a diameter of the second distal lumen.

19. The method of claim 18, wherein the first proximal lumen, the intermediate lumen, and the first distal lumen define an inflation lumen, wherein a distal end of the first distal lumen is closed, and wherein the blocking mechanism comprises a flexible wall defining the first distal lumen.

20. The method of claim 19, wherein the step of preventing the distal portion of the guidewire from translating comprises injecting an inflation fluid into the first distal lumen such that the flexible wall expands to impinge on the guidewire in the second distal lumen.

21. The method of claim 18, wherein the blocking mechanism comprises a balloon disposed at the first distal lumen.

22. The method of claim 21, wherein the step of preventing the distal portion of the guidewire from translating comprises injecting an inflation fluid into the first distal lumen such that the balloon expands to impinge on the guidewire in the second distal lumen.

23. The method of claim 18, wherein the blocking mechanism comprises a mechanical arm, and wherein the step of preventing the distal portion of the guidewire from translating comprises activating the mechanical arm.

24. The method of claim 23, wherein the catheter further comprises a mechanical mechanism configured to activate the mechanical arm, wherein the mechanical mechanism extends proximally from the mechanical arm.

25. The method of claim 18, wherein the distal portion of the catheter comprises a distal guidewire shaft defining the second distal lumen and the blocking mechanism comprises a distal outer tube surrounding the distal guidewire shaft such that the first distal lumen is an annular inflation lumen defined between an outer surface of the distal guidewire shaft and an inner surface of the distal outer tube.

26. The method of claim 25, wherein the step of preventing the distal portion of the guidewire from translating comprises injecting an inflation fluid into the first distal lumen such that the distal guidewire shaft compresses radially to reduce the diameter of the second distal lumen.

27. The method of claim 15, wherein the catheter further comprises a second proximal lumen, and wherein when the catheter is advanced over the guidewire, the guidewire is also disposed in the second proximal lumen.

* * * * *